(12) United States Patent
Valkirs et al.

(10) Patent No.: US 7,985,560 B2
(45) Date of Patent: Jul. 26, 2011

(54) METHODS AND COMPOSITIONS FOR MONITORING AND RISK PREDICTION IN CARDIORENAL SYNDROME

(75) Inventors: Gunars Valkirs, Lahaina, HI (US); Paul H. McPherson, Encinitas, CA (US)

(73) Assignee: Alere San Diego, Inc., San Diego, CA (US)

( * ) Notice: Subject to any disclaimer, the term of this patent is extended or adjusted under 35 U.S.C. 154(b) by 0 days.

(21) Appl. No.: 12/909,654

(22) Filed: Oct. 21, 2010

(65) Prior Publication Data

US 2011/0104726 A1    May 5, 2011

Related U.S. Application Data

(62) Division of application No. 11/940,111, filed on Nov. 14, 2007, now Pat. No. 7,842,472.

(60) Provisional application No. 60/891,342, filed on Feb. 23, 2007, provisional application No. 60/859,137, filed on Nov. 14, 2006.

(51) Int. Cl.
*G01N 1/00* (2006.01)
*G01N 33/53* (2006.01)

(52) U.S. Cl. ............ 435/7.21; 435/2; 435/7.1; 436/501; 436/518; 436/522; 422/50

(58) Field of Classification Search .................. None
See application file for complete search history.

(56) References Cited

U.S. PATENT DOCUMENTS

| | | | |
|---|---|---|---|
| 4,900,662 A | 2/1990 | Shah et al. |
| 5,202,234 A | 4/1993 | Shah et al. |
| 5,382,515 A | 1/1995 | Shah et al. |
| 5,382,522 A | 1/1995 | Shah et al. |
| 5,480,792 A | 1/1996 | Buechler et al. |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,763,189 A | 6/1998 | Buechler et al. |
| 5,795,725 A | 8/1998 | Buechler et al. |
| 5,824,799 A | 10/1998 | Buechler et al. |
| 5,843,690 A | 12/1998 | Gargan |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,113,855 A | 9/2000 | Buechler et al. |
| 6,143,576 A | 11/2000 | Buechler |
| 6,156,521 A | 12/2000 | Buechler et al. |
| 6,174,686 B1 | 1/2001 | Buechler et al. |
| 6,238,931 B1 | 5/2001 | Buechler et al. |
| 6,251,687 B1 | 6/2001 | Buechler et al. |
| 6,316,409 B1 | 11/2001 | Neri et al. |
| 6,579,687 B1 | 6/2003 | Buechler et al. |
| 6,627,404 B1 | 9/2003 | Buechler et al. |
| 6,939,678 B1 | 9/2005 | Buechler et al. |
| 6,991,907 B1 | 1/2006 | Buechler et al. |
| 7,341,838 B2 | 3/2008 | Buechler et al. |
| 7,358,055 B2 | 4/2008 | Valkirs et al. |
| 7,361,473 B2 | 4/2008 | Valkirs et al. |
| 7,427,490 B2 | 9/2008 | Valkirs |
| 7,842,472 B2 | 11/2010 | Valkirs et al. |
| 2003/0022235 A1 | 1/2003 | Dahlen et al. |
| 2003/0119064 A1 | 6/2003 | Valkirs et al. |
| 2003/0199000 A1 | 10/2003 | Valkirs et al. |
| 2003/0211544 A1 | 11/2003 | Buechler et al. |
| 2003/0219734 A1 | 11/2003 | Buechler |
| 2004/0121343 A1 | 6/2004 | Buechler et al. |
| 2004/0121350 A1 | 6/2004 | Anderberg et al. |
| 2004/0126767 A1 | 7/2004 | Anderberg et al. |
| 2004/0171064 A1 | 9/2004 | Dahlen et al. |
| 2004/0176914 A1 | 9/2004 | Buechler et al. |
| 2004/0203083 A1 | 10/2004 | Buechler et al. |
| 2004/0209307 A1 | 10/2004 | Valkirs et al. |
| 2004/0219509 A1 | 11/2004 | Valkirs et al. |
| 2004/0219603 A1 | 11/2004 | Devarajan et al. |
| 2004/0253637 A1 | 12/2004 | Buechler et al. |
| 2005/0148024 A1 | 7/2005 | Buechler |
| 2005/0164317 A1 | 7/2005 | Buechler et al. |
| 2005/0255484 A1 | 11/2005 | Valkirs et al. |
| 2006/0051825 A1 | 3/2006 | Buechler et al. |
| 2006/0105419 A1 | 5/2006 | Blankenberg et al. |
| 2007/0092911 A1 | 4/2007 | Buechler et al. |

(Continued)

FOREIGN PATENT DOCUMENTS

WO    WO 93/24231 A1    12/1993

(Continued)

OTHER PUBLICATIONS

U.S. Appl. No. 60/436,392, filed Dec. 24, 2002, Anderberg et al.
Anderson, L. Candidate-Based Proteomics in the Search for Biomarkers of Cardiovascular Disease. J. Physiol. 563.1; 2004: 23-60.
Bachorzewska, et al. Neutrophil gelatinase-associated lipocalin (NGAL) correlations with cystatin C, serum creatinine and eGFR in patients with normal serum creatinine undergoing coronary angiography. Nephrol. Dial. Transplant. 2007;(22):295-296.
Boerrigter, et al. Des-Serine-Proline B-Type Natriuretic Peptide (BNP 3-32) in Cardiorenal Regulation. Am J Physiol Regul Integr Comp Physiol (Oct. 26, 2006).

(Continued)

*Primary Examiner* — Lisa Cook
(74) *Attorney, Agent, or Firm* — Wilson Sonsini Goodrich & Rosati

(57) ABSTRACT

The present invention relates to methods and compositions for monitoring, diagnosis, prognosis, and determination of treatment regimens in subjects. In particular, the invention relates to methods and compositions selected to monitor cardiorenal syndrome using assays that detect NGAL, preferably together with assays that detect natriuretic peptides such as BNP. Such methods and compositions can provide early indications of a deterioration in cardiorenal syndrome status, including prognosis regarding mortality and worsening renal function.

3 Claims, No Drawings

U.S. PATENT DOCUMENTS

| | | |
|---|---|---|
| 2007/0196880 A1 | 8/2007 | Buechler et al. |
| 2007/0218498 A1 | 9/2007 | Buechler et al. |
| 2007/0224643 A1 | 9/2007 | McPherson et al. |
| 2007/0269836 A1 | 11/2007 | McPherson |
| 2008/0045444 A1 | 2/2008 | Whittaker |
| 2008/0050832 A1 | 2/2008 | Buechler et al. |
| 2008/0118924 A1 | 5/2008 | Buechler |
| 2008/0254485 A1 | 10/2008 | Valkirs et al. |
| 2008/0293920 A1 | 11/2008 | Buechler |
| 2009/0061467 A1 | 3/2009 | Buechler et al. |
| 2010/0086944 A1 | 4/2010 | Valkirs et al. |

FOREIGN PATENT DOCUMENTS

| | | | |
|---|---|---|---|
| WO | WO 95/08772 A1 | 3/1995 | |
| WO | WO 98/08606 A2 | 3/1998 | |
| WO | WO 98/21563 A1 | 5/1998 | |
| WO | WO 98/08606 A3 | 7/1998 | |
| WO | WO 98/43739 A2 | 10/1998 | |
| WO | WO 98/43739 A3 | 6/2001 | |
| WO | WO 2004/058055 A2 | 7/2004 | |
| WO | WO 2004/058055 A3 | 7/2004 | |
| WO | WO 2004/059293 A2 | 7/2004 | |
| WO | WO 2004/088276 A2 | 10/2004 | |
| WO | WO 2004/088276 A3 | 11/2004 | |
| WO | WO 2004/059293 A3 | 3/2005 | |
| WO | WO 2005/121788 A2 | 12/2005 | |
| WO | WO 2005/121788 A3 | 5/2006 | |
| WO | WO 2006/066587 A1 | 6/2006 | |
| WO | WO 2008/061149 A2 | 5/2008 | |
| WO | WO 2008/061149 A3 | 10/2008 | |

OTHER PUBLICATIONS

Buechler, K. Chapter 41, entitled "Near Patient Tests: Triage Cardiac System," in The Immunoassay Handbook, 2nd ed., David Wild, ed., Nature Publishing Group, 2001.

Cataliotti, et al. Circulating Natriuretic Peptide Concentrations in Patients with End-Stage Renal Disease: Role for Brain Natriuretic Peptide as a Biomarker for Ventricular Remodeling. Mayo Clin. Proc. 2001;76:1111-1119.

Chen et al. The Natriuretic Peptides in Heart Failure: Diagnostic and Therapeutic Potentials. Proceedings of the Assoc of American Physicians. Sep./Oct. 1999; 111(5):406-416.

Cwirla, et al. Peptides on Phage: A Vast Library of Peptides for Identifying Ligands Proc. Natl. Acad. Sci. USA 87:6378-6382 (1990).

Dangas et al. Contrast-induced nephropathy after percutaneous coronary interventions in relation to chronic kidney disease and hemodynamic variables. Am J. Cariol. Jan. 1, 2005;95(1):13-9.

Davis et al. Genomic based biomarkers of drug-induced nephrotoxicity. Expert Opin Drug Metab Toxicol. Feb. 2006;2(1):95-101.

Devlin, et al. Random Peptide Libraries: A Source of Specific Protein Binding Molecules Science 249:404-406 (1990).

Fischer et al. Uncomplicated acute renal failure and hospital resource utilization: a retrospective multicenter analysis. Am J Kidney Dis. Dec. 2005;46(6):1049-57.

Fischer, et al. A readers' guide to the interpretation of diagnostic test properties: clinical example of sepsis. Intensive Care Med. Intensive Care Med. Jul. 2003;29(7):1043-51.

Francis, G. Acute decompensated heart failure; the cardiorenal syndrome. Cleve Clin J Med. Jun. 2006;73 Suppl 2:S8-13; discussion S30-3.

Fujiwara, et al. Synthesis of Human C-Type Natriuretic Peptide 22 Using Chlorotrityl Resin and Tetrafluoroboric Acid Deprotection Chem. Pharm. Bull. (Tokyo) 44:1326-1331 (1996).

Goetze et al. Quantification of pro-B-type natriuretic peptide and its products in human plasma by use of an analysis independent of precursor processing. Clin. Chem. 2002; 48:1035-42.

Gottschling, et al. Cellular solid-phase binding assay and mass spectrometry for screening of alpha 4 beta 7 integrin antagonists. Bioorg Med Chem Lett. Dec. 3, 2001;11(23):2997-3000.

Gruberg et al. The prognostic implications of further renal function deterioration within 48 hours of interventional coronary procedures in patients with pre-existent chronic renal insufficiency.J Am Coll Cardiol. Nov. 1, 2000;36(5):1542-8.

Hanley, et al. The Meaning and Use of the Area under a Receiver Operating Characteristic (ROC) Curve. Radiology 1982;143: 29-36.

Huse, et al. Application of a Filamentous Phage pVIII Fusion Protein System Suitable for Efficient Production, Screening, and Mutagenesis of F(ab) Antibody Fragments J. Immunol. 149:3914-3920 (1992).

International Search Report dated Feb. 13, 2008 from PCT Application No. US 2006/038755.

Kiso, et al, Solution-Phase Synthesis of Porcine Brain Natriuretic Peptide (pBNP) Using S-Trimethylactamido-Methycystein Chem. Pharm. Bull. (Tokyo) 38:1192-1199 (1990).

Leon, et al. Evaluation of resins for on-bead screening: a study of papain and chymotrypsin specificity using PEGA-bound combinatorial peptide libraries. Bioorg Med Chem Lett. Nov. 3, 1998;8(21):2997-3002.

Levey, et al. A more accurate method to estimate glomerular filtration rate from serum creatinine: a new prediction equation. Modification of Diet in Renal Disease Study Group. Ann Intern Med. Mar. 16, 1999;130(6):461-70.

Mahon et al. Perioperative acute renal failure. Curr Opin Anaesthesiol. Jun. 2006;19(3):332-8.

McCullough et al. Risk prediction of contrast-induced nephropathy. Am J Cardiol. Sep. 18, 2006;98(6A):27K-36K.

McCullough P.A. Beyond Serum Creatinine: Defining the Patient with Renal Insufficiency and Why? Reviews in Cardiovascular Medicine. 2003; 4(1): 82-86.

Mehran et al. A simple risk score for prediction of contrast-induced nephropathy after percutaneous coronary intervention: development and initial validation. J Am Coll Cardiol. Oct. 6, 2004;44(7):1393-9.

Mostafavi, et al. Synthesis, Purification and Biological Activity of (SER10-Phosphatidyl)-Urodilatin (Phosphourodilatin) Biomed. Pept. Proteins Nucleic Acids 1:255-260 (1995).

Nelson et al. A Computer Program for Calculating Antibody Affinity Constants. Computer Methods Programs Biomed. 27:65-68 (1988).

Ng, et al. Biomedical applications of protein chips. J Cell Mol Med. Jul.-Sep. 2002;6(3):329-40.

Ok et al. Carbamylated low-density lipoprotein induces death of endothelial cells: a link to atherosclerosis in patients with kidney disease. Kidney International. 1995; 68:173-78.

Orain, et al. Solid phase synthesis of trypanothione reductase inhibitors—towards single bead screening. Tetrahedron Letters. vol. 42, Issue 3, Jan. 15, 2001, pp. 515.518.

Papanikos, et al. Alpha-Ketocarbonyl peptides: a general approach to reactive resin-bound intermediates in the synthesis of peptide isosteres for protease inhibitor screening on solid support. J Am Chem Soc. Mar. 14, 2001;123(10):2176-81.

Parmley, et al. Antibody-selectable filamentous fd phage vectors: affinity purification of target genes. Gene. 1988; 73(2):305-318.

Permberton, et al. Deconvolution Analysis of Cardiac Natriuretic Peptides During Acute Volume Overload. Hypertension. Sep. 2000; 355-359.

Persson et al. Pathophysiology of contrast medium-induced nephropathy. Kidney Int. Jul. 2005;68(1):14-22.

Persson, PB. Contrast-induced nephropathy. Eur Radiol. Nov. 2005;15 Suppl 4:D65-9.

Savonitto, et al. Prognostic Value of the Admission Electrocardiogram in Acute Coronary Syndromes. JAMA 1999 28I:707-713.

Sawicki, et al. Localization and Translocation of MMP-2 during Aggregation of Human Platelets. Thromb. Haemost. 1998;80:836-839.

Schneider et al. Association of selective and conventional nonsteroidal antiinflammatory drugs with acute renal failure: A population-based, nested case-control analysis. Am J Epidemiol. Nov. 1, 2006;164(9):881-9.

Scott, et al. Searching for Peptide Ligands with an Epitope Library. Science 249:386-388 (1990).

Sharma et al. TGF-β in diabetic kidney disease: role of novel signaling pathways. Cytokine Growth Factor Rev. Mar.-Jun. 2000;11(1-2):115-23.

Shur, B. The receptor function of galactosyltransferase during cellular interactions. Mol Cell Biochem. 1984;61(2):143-58.

Simpson, D. Controversies in the estimation of glomerular filtration rate. Nucl Med Commun. Apr. 2006;27(4):407.

Smith, et al. Comparison of resin and solution screening methodologies in combinatorial chemistry and the identification of a 100 nM inhibitor of trypanothione reductase. J Comb Chem. Jul.-Aug. 1999;1(4):326-32.

Stacul et al. Strategies to reduce the risk of contrast-induced nephropathy. Am J Cardiol. Sep. 18, 2006;98(6A):59K-77K.

Taber et al. Drug-Associated Renal Dysfunction. Crit Care Clin. Apr. 2006;22(2):357-74, viii.

The Merck Manual of Diagnosis and Terapy, 17th Ed. Merck & Co., Inc. 1999, pp. 1629-1648.

Van Erp, et al. Application of a Sol Particle Immunoassay to the Determination of Affinity Constants of Monoclonal Antibodies J. Immunoassay 1991;12:425-443.

Ward, et al. Binding Activities of a Repertoire of Single Immunoglobulin Variable Domains Secreted from *Escherichia coli*. Nature 341:544-546 (1989).

Wilson, et al. Simplified Conjugation Chemistry for Coupling Peptides to F(ab') Fragments: Autologous Red Cell Agglutination Assay for HIV-1 Antibodies J. Immunol. Methods 175:267-273 (1994).

Yarmush, et al. Coupling of Antibody-binding fragments to solid-phase supports: site-directed binding of F(ab)2 fragments. J Biochem. Biophys. Methods 1992 5:85-97.

International search report dated Aug. 5, 2008 for PCT Application No. US2007/024033.

SEQUENCE LISTING

<160> NUMBER OF SEQ ID NOS: 2

<210> SEQ ID NO 1
<211> LENGTH: 108
<212> TYPE: PRT
<213> ORGANISM: Homo sapiens

```
-continued

<400> SEQUENCE: 1

His Pro Leu Gly Ser Pro Gly Ser Ala Ser Asp Leu Glu Thr Ser Gly
1               5                  10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 2
<211> LENGTH: 134
<212> TYPE: PRT
<213> ORGANISM: Homo sapiens

<400> SEQUENCE: 2

Met Asp Pro Gln Thr Ala Pro Ser Arg Ala Leu Leu Leu Leu Leu Phe
1               5                  10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
            115                 120                 125

Lys Val Leu Arg Arg His
        130
```

METHODS AND COMPOSITIONS FOR MONITORING AND RISK PREDICTION IN CARDIORENAL SYNDROME

CROSS-REFERENCE TO RELATED APPLICATIONS

This application is a division of U.S. application Ser. No. 11/940,111 filed Nov. 14, 2007 now U.S. Pat. No. 7,842,472, which claims benefit under 35 U.S.C. §119(e) of U.S. Application No. 60/891,342 filed Feb. 23, 2007 and U.S. Application No. 60/859,137 filed Nov. 14, 2006, both of which are incorporated by reference herein for all purposes.

SEQUENCE LISTING

The instant application contains a Sequence Listing which has been submitted in ASCII format via EFS-Web and is hereby incorporated by reference in its entirety. Said ASCII copy, created on Dec. 28, 2010, is named 36671779401.txt and is 3 Kilobytes in size.

FIELD OF THE INVENTION

The present invention relates to methods and compositions for monitoring cardiorenal syndrome, and the heart failure and renal dysfunction underlying cardiorenal syndrome.

BACKGROUND OF THE INVENTION

The following discussion of the background of the invention is merely provided to aid the reader in understanding the invention and is not admitted to describe or constitute prior art to the present invention.

The term "cardiorenal syndrome" refers to a physiologic relationship between the heart and kidney that manifests as a tight coordination between renal and cardiac functions in subjects suffering from heart failure. While the syndrome is poorly understood, a feedback loop amongst neurohormonal systems (and, in particular, the natriuretic peptides), inflammatory responses, and structurally and functionally impaired organs has been implicated, creating a cycle of worsening cardiac and renal functions. A recent discussion of cardiorenal syndrome may be found in Francis, "Acute decompensated heart failure: The cardiorenal syndrome," Clev. Clinic J. Med. 73(S2): S8-S13, 2006.

In heart failure patients, the onset of renal dysfunction has proved a strong risk factor for mortality. In fact, an increased risk is signaled even at serum creatinine levels >1.3 mg/dL and estimated creatinine clearance values ≦60 to 70 mL/min, values that can fall within "normal" values for each of these parameters. Although renal dysfunction predicts all-cause mortality, it is most predictive of death from progressive heart failure, which suggests that it is a manifestation of and/or exacerbating factor for left ventricular dysfunction. And worsening renal function may be even more important than baseline renal function for predicting adverse outcomes. In one multicenter study, a serum creatinine increase of ≧0.3 mg/dL had a sensitivity of 65% and specificity of 81% for predicting in-hospital mortality. Gottlieb et al., "The prognostic importance of different definitions of worsening renal function in congestive heart failure," J. Card. Fail. 8: 136-141, 2002. Other studies have reported that deteriorating renal function is associated with a longer length of stay, an increased risk of death within 6 months after discharge, and a 33% increased risk for hospital readmission.

In addition, numerous studies have demonstrated that a variety of heart failure therapies may actually worsen renal function, triggering a deterioration in the cardiorenal axis. For example, certain diuretics have been associated with worsening renal function, especially in the presence of ACE inhibitors, and high diuretic doses have been associated with increased mortality rates. This is often thought to result from "diuretic resistance," e.g., a failure to excrete at least 90 mmol of sodium within 72 hours of a 160 mg oral furosemide dose given twice daily, which necessitates increasing diuretic dosage. Whatever the cause, the resulting volume overload is poorly tolerated and a frequent cause of hospital admission in patients with heart failure.

In patients exhibiting worsening renal function, volume overload, and diuretic refractoriness, the management of cardiorenal disease can be extremely difficult. Positive inotropic agents (including dobutamine, phosphodiesterase inhibitors, and levosimendan) may facilitate a diuresis with preservation or improvement in renal function. Although dopamine also is used because of its presumed ability to improve renal blood flow, this effect is severely limited in advanced heart failure. Intravenous vasodilators can improve hemodynamics, but often will not improve renal function.

In recent years, natriuretic peptide measurement has dramatically changed the diagnosis and management of cardiac diseases, including heart failure and the acute coronary syndromes. In particular, B-type natriuretic peptide (BNP, human precursor Swiss-Prot P16860), and various related polypeptides arising from the common precursor proBNP, have been used to diagnose heart failure, determine its severity, and estimate prognosis. In addition, BNP and its related polypeptides have been demonstrated to provide diagnostic and prognostic information in unstable angina, non-ST-elevation myocardial infarction, and ST-elevation myocardial infarction.

In contrast, current diagnostic tests for renal dysfunction, such as serum creatinine or cystatin C measurements, can be misleading to the clinician. While it is preferred that aggressive treatment begin at the earliest indication of renal dysfunction, these tests may only become abnormal days after the original insult. A large proportion of the renal mass may be damaged before any biochemical evidence of renal dysfunction is appreciated, as the rise of serum creatinine may not be evident before 50% of the glomerular filtration rate is lost. No surprisingly perhaps, it has been reported that about two thirds of the patients admitted for acute heart failure have inadequate glomerular filtration rates or creatinine clearance, despite relatively normal serum creatinine levels. Recently, NGAL (also known as neutrophil gelatinase-associated lipocalin, human precursor Swiss-Prot P80188) has been proposed as a new early marker for acute renal injury, with reports of increased levels of NGAL from acute renal injury detectable in both urine and blood within two hours of the insult. See, e.g., WO04088276; WO05121788; WO06066587. The use of NGAL as a risk marker in the context of heart failure, renal dysfunction, or cardiorenal syndrome has not been described.

BRIEF SUMMARY OF THE INVENTION

It is an object of the invention to provide methods and compositions for diagnosis, prognosis, and determination of treatment regimens in subjects suffering from renal dysfunction, heart failure, and cardiorenal syndrome. In various aspects, the present invention provides methods for assessing risk of worsening renal function in the context of heart failure; methods for assigning risk of mortality in the context of renal dysfunction, methods of monitoring cardiorenal syndrome; and various devices and kits adapted to perform such methods.

In a first aspect, the present invention relates to methods for assigning a risk of worsening renal function to a patient suffering from heart failure. These methods comprise performing an assay method that configured to detect NGAL (and/or one or more markers related thereto, as that term is defined herein) on a body fluid sample obtained from a subject suffering from heart failure. The assay result (referred to herein as an "NGAL assay result," which may be expressed in the form of an NGAL concentration) is compared to a baseline NGAL result, and an increased risk of worsening renal function is assigned to the subject when the NGAL assay result is above the baseline, relative to a risk assigned when the NGAL assay result is below the baseline. In the alternative, a decreased risk of worsening renal function is assigned to the subject when the NGAL assay result is below the baseline, relative to a risk assigned when the NGAL assay result is above than the baseline.

In a related aspect, the present invention relates to methods for assigning a risk of an adverse outcome to a patient suffering from heart failure. These methods comprise performing an assay method configured to detect NGAL (and/or one or more markers related thereto, as that term is defined herein) on a body fluid sample obtained from a subject suffering from heart failure. The assay result (referred to herein as an "NGAL assay result," which may be expressed in the form of an NGAL concentration) is compared to a baseline NGAL result, and an increased risk of one or more adverse outcomes is assigned to the subject when the NGAL assay result is above the baseline, relative to a risk assigned when the NGAL assay result is below the baseline. In the alternative, a decreased risk of one or more adverse outcomes is assigned to the subject when the NGAL assay result is below the baseline, relative to a risk assigned when the NGAL assay result is above the baseline. As described hereinafter, preferred adverse outcomes are mortality and/or an acute cardiac event requiring immediate medical care. Preferred acute cardiac events are symptoms resulting from heart failure or an acute coronary syndrome, such a chest pain and/or dyspnea.

A variety of methods may be used by the skilled artisan to arrive at a desired baseline. In certain preferred embodiments, the baseline NGAL result is determined from an earlier NGAL assay result obtained from the same subject. That is, the change in NGAL concentration may be observed over time, and an increased NGAL concentration provides an indication of worsening renal function in the heart failure patient.

In alternative embodiments, the baseline NGAL result is determined from a population of subjects suffering from heart failure as described hereinafter, and is based on an NGAL result that can provide an acceptable level of specificity and sensitivity in separating the population into a "first" subpopulation (e.g., having an increased risk of worsening (or improving) renal function or an increased risk of an adverse outcome) relative to the remaining "second" subpopulation. As discussed herein, a preferred baseline NGAL result separates this first and second population by one or more of the following measures of test accuracy:

an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less.

at least 75% sensitivity, combined with at least 75% specificity;

a ROC curve area of at least 0.6, more preferably 0.7, still more preferably at least 0.8, even more preferably at least 0.9, and most preferably at least 0.95; and/or a positive likelihood ratio (calculated as sensitivity/(1−specificity)) of at least 5, more preferably at least 10, and most preferably at least 20; or a negative likelihood ratio (calculated as (1−sensitivity)/specificity) of less than or equal to 0.3, more preferably less than or equal to 0.2, and most preferably less than or equal to 0.1.

The term "about" in this context refers to +/−5% of a given measurement.

The present methods preferably assign a "near-term" risk of worsening renal function and/or risk of an adverse outcome. By "near term" is meant within 30 days. As described hereinafter, the methods preferably assign a risk of worsening renal function and/or mortality within 7 days, more preferably within 5 days, and still more preferably within 3 days.

Preferred assay methods comprise performing an immunoassay that detects NGAL. Antibodies for use in such assays will specifically bind NGAL, and may optionally also bind one or more polypeptides that are "related" thereto, as described hereinafter with regard to related markers. Such immunoassays may comprise contacting said body fluid sample with a solid phase comprising antibody that detects NGAL, and detecting binding to said antibody, although assay formats that do not require the use of a solid phase are known in the art. Preferably, the body fluid sample is selected from the group consisting of urine, blood, serum, and plasma.

In addition to NGAL assay results, additional variables may be included in the methods for assigning a risk of worsening renal function and/or risk of an adverse outcome described herein. As described in additional detail hereinafter, assays that detect various markers (both subject-derived and physical characteristics) may be combined, including assays that detect various natriuretic peptides such as BNP, NT-proBNP, and proBNP; markers related to inflammation such as myeloperoxidase, soluble FLT-1, C-reactive protein, and placental growth factor; markers related to cardiac damage such as cardiac troponins and CK-MB; markers of renal damage such as serum creatinine, creatinine clearance rates, cystatin C, and glomerular filtration rates; and variables such as urine output levels, age, the presence or absence of various cardiovascular risk factors such as diabetes, hypertension, body mass, smoking status; etc. In these "multiple marker" methods, the patient's risk of worsening renal function or risk of an adverse outcome is assigned based both on comparing the NGAL assay result to the baseline NGAL result as described above, and on one or more of these additional variables. In many cases, these additional variables can be used in a manner analogous to NGAL, in that baseline results can be established for these markers as described herein for comparison of a test result measured on a body fluid sample. In other cases, such as sex, cardiovascular risk factors, etc., the variables can be dichotomized for analysis of risk. For example, different NGAL baselines may be established for different age groups, and/or based on sex of the subject.

In methods where multiple assays are performed on body fluids, the various assays can be performed on the same or different body fluid samples. For example, NGAL may be measured in a urine sample and BNP may be measured in a plasma sample; or NGAL may be measured in a plasma sample and cystatin C measured in a different plasma sample.

In another aspect, the present invention relates to methods for assigning a risk of mortality to a patient suffering from renal dysfunction. These methods comprise performing an assay method that configured to detect NGAL (and/or one or more markers related thereto, as that term is defined herein) on a body fluid sample obtained from a subject suffering from renal dysfunction. The assay result (referred to herein as an "NGAL assay result," which may be expressed in the form of an NGAL concentration) is compared to a baseline NGAL result, and an increased mortality risk is assigned to the subject when the NGAL assay result is above the baseline, relative to a risk assigned when the NGAL assay result is below the baseline. In the alternative, a decreased mortality risk is assigned to the subject when the NGAL assay result is below the baseline, relative to a risk assigned when the NGAL assay result is above than the baseline.

As discussed above, a variety of methods may be used by the skilled artisan to arrive at a desired baseline. In certain preferred embodiments, the baseline NGAL result is determined from an earlier NGAL assay result obtained from the same subject. That is, the change in NGAL concentration may be observed over time, and an increased NGAL concentration provides an indication of worsening renal function in the heart failure patient.

In alternative embodiments, the baseline NGAL result is determined from a population of subjects suffering from renal dysfunction as described hereinafter, and is based on an NGAL result that can provide an acceptable level of specificity and sensitivity in separating the population into a "first" subpopulation having an increased (or decreased) mortality risk relative to the remaining "second" subpopulation. As discussed herein, a preferred baseline NGAL result separates this first and second population by one or more of the following measures of test accuracy:

an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less.

at least 75% sensitivity, combined with at least 75% specificity;

a ROC curve area of at least 0.6, more preferably 0.7, still more preferably at least 0.8, even more preferably at least 0.9, and most preferably at least 0.95; and/or a positive likelihood ratio (calculated as sensitivity/(1−specificity)) of at least 5, more preferably at least 10, and most preferably at least 20; or a negative likelihood ratio (calculated as (1−sensitivity)/specificity) of less than or equal to 0.3, more preferably less than or equal to 0.2, and most preferably less than or equal to 0.1.

The term "about" in this context refers to +/−5% of a given measurement.

The present methods preferably assign a "near-term" mortality risk. By "near term" is meant within 30 days. As described hereinafter, the methods preferably assign a mortality risk within 7 days, more preferably within 5 days, and still more preferably within 3 days.

As is also described above, preferred assay methods comprise performing an immunoassay that detects NGAL. Antibodies for use in such assays can specifically bind NGAL, and may optionally also bind one or more polypeptides that are "related" thereto. Such immunoassays may comprise contacting said body fluid sample with a solid phase comprising antibody that detects NGAL, and detecting binding to said antibody, although assay formats that do not require the use of a solid phase are known in the art. Preferably, the body fluid sample is selected from the group consisting of urine, blood, serum, and plasma.

In addition to NGAL assay results, additional variables may be included in the methods for assigning a mortality risk in the context of renal dysfunction. As described in additional detail hereinafter, assays that detect various markers (both subject-derived and physical characteristics) may be combined, including assays that detect various natriuretic peptides such as BNP, NT-proBNP, and proBNP; markers related to inflammation such as myeloperoxidase, soluble FLT-1, C-reactive protein, and placental growth factor; markers related to cardiac damage such as cardiac troponins and CK-MB; markers of renal damage such as serum creatinine, creatinine clearance rates, cystatin C, and glomerular filtration rates; and variables such as urine output levels, age, the presence or absence of various cardiovascular risk factors such as diabetes, hypertension, body mass, smoking status; etc. In these "multiple marker" methods, the patient's mortality risk is assigned based both on comparing the NGAL assay result to the baseline NGAL result as described above, and on one or more of these additional variables. In many cases, these additional variables can be used in a manner analogous to NGAL, in that baseline results can be established for these markers as described herein for comparison of a test result measured on a body fluid sample. In other cases, such as sex, cardiovascular risk factors, etc., the variables can be dichotomized for analysis of risk. For example, different NGAL baselines may be established for different age groups, and/or based on sex of the subject.

As noted above, the various assays can be performed on the same or different body fluid samples. For example, NGAL may be measured in a urine sample and BNP may be measured in a plasma sample; or NGAL may be measured in a plasma sample and cystatin C measured in a different plasma sample.

In still another aspect, the present invention relates to methods for monitoring cardiorenal syndrome in a patient. These methods comprise performing an assay method that configured to detect NGAL and an assay method configured to detect one or more of BNP, NT-proBNP and proBNP (and/or one or more markers related thereto in each case, as that term is defined herein) on a body fluid sample obtained from a subject. Each of the assay results (referred to herein as an "NGAL assay result," which may be expressed in the form of an NGAL concentration, and a "natriuretic peptide result," which may be expressed in the form of a concentration of one or more of BNP, NT-proBNP and proBNP) is compared to a corresponding baseline result—that is, a baseline NGAL result and a baseline natriuretic peptide result. A worsening cardiorenal syndrome status may be assigned to the patient if either or both of the assay results are greater than the corresponding baseline result. In the alternative, an improving cardiorenal syndrome status may be assigned to the patient if either or both of the assay results are less than the corresponding baseline result.

As in the previous aspects, a variety of methods may be used by the skilled artisan to arrive at each desired baseline values. In certain preferred embodiments, the baseline result is determined from an earlier assay result obtained from the same subject. In alternative embodiments, the baseline result is determined from a population of subjects, and is based on an assay result that can provide an acceptable level of specificity and sensitivity in separating the population into a "first" subpopulation having a worsening (or improving) cardiorenal syndrome status relative to the remaining "second" subpopulation.

As discussed herein, a preferred baseline result separates this first and second population by one or more of the following measures of test accuracy:

an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less.

at least 75% sensitivity, combined with at least 75% specificity;

a ROC curve area of at least 0.6, more preferably 0.7, still more preferably at least 0.8, even more preferably at least 0.9, and most preferably at least 0.95; and/or a positive likelihood ratio (calculated as sensitivity/(1-specificity)) of at least 5, more preferably at least 10, and most preferably at least 20; or a negative likelihood ratio (calculated as (1-sensitivity)/specificity) of less than or equal to 0.3, more preferably less than or equal to 0.2, and most preferably less than or equal to 0.1.

The term "about" in this context refers to +/-5% of a given measurement.

The present methods preferably assign a "near-term" change in cardiorenal syndrome status. By "near term" is meant within 30 days. As described hereinafter, the methods preferably assign a mortality risk within 7 days, more preferably within 5 days, and still more preferably within 3 days.

As is also described above, preferred assay methods comprise performing an immunoassay that detects NGAL and/or an immunoassay that detects one or more of BNP, NT-proBNP and proBNP. Antibodies for use in such assays can specifically bind to the intended target(s) of the assay, and may optionally also bind one or more polypeptides that are "related" thereto. Such immunoassays may comprise contacting said body fluid sample with a solid phase comprising antibody that detects the intended target(s), and detecting binding to said antibody, although assay formats that do not require the use of a solid phase are known in the art. Preferably, the body fluid sample is selected from the group consisting of urine, blood, serum, and plasma.

Additional variables may be included in the methods for assigning a mortality risk in the context of renal dysfunction. As described in additional detail hereinafter, assays that detect various markers (both subject-derived and physical characteristics) may be combined, including assays that detect various natriuretic peptides other than BNP, NT-proBNP, and proBNP; markers related to inflammation such as myeloperoxidase, soluble FLT-1, C-reactive protein, and placental growth factor; markers related to cardiac damage such as cardiac troponins and CK-MB; markers of renal damage such as serum creatinine, creatinine clearance rates, cystatin C, and glomerular filtration rates; and variables such as urine output levels, age, the presence or absence of various cardiovascular risk factors such as diabetes, hypertension, body mass, smoking status; etc.

As noted above, the various assays can be performed on the same or different body fluid samples. For example, NGAL may be measured in a urine sample and BNP may be measured in a plasma sample; or NGAL may be measured in a plasma sample and BNP measured in a different plasma sample.

In various related aspects, the present invention relates to devices and kits for performing the methods described herein. Suitable kits comprise reagents sufficient for performing at least one of the described assays, together with instructions for performing the described baseline comparisons. In the case of assigning a risk of worsening renal function, such instructions can include instructions for obtaining the described NGAL baseline result, and/or for assigning a risk of worsening renal function based on the results of the comparison, and such kits can optionally include comparable reagents and instructions for measuring and using additional variables such as BNP, NT-proBNP, and proBNP, etc., as described above. In the case of assigning a risk of mortality, such instructions can include instructions for obtaining the described NGAL baseline result, and/or for assigning a risk of mortality based on the results of the comparison, and such kits can optionally include comparable reagents and instructions for measuring and using additional variables such as BNP, NT-proBNP, and proBNP, etc., as described above. In the case of monitoring cardiorenal syndrome, such instructions can include instructions for obtaining the described NGAL and natriuretic peptide baseline results, and/or for assigning a change in cardiorenal syndrome status based on the results of the comparisons, and such kits can optionally include comparable reagents and instructions for measuring and using additional variables such as various natriuretic peptides other than BNP, NT-proBNP, and proBNP, etc., as described above.

In certain embodiments, reagents for performing such assays are provided in an assay device, and such assay devices may be included in such a kit. Preferred reagents comprise one or more solid phase antibodies, the solid phase antibody comprising antibody that detects the intended target(s) bound to a solid support. In the case of sandwich immunoassays, such reagents can also include one or more detectably labeled antibodies, the detectably labeled antibody comprising antibody that detects the intended target(s) bound to a detectable label. Additional optional elements that may be provided as part of an assay device are described hereinafter. A preferred assay device comprises reagents for performing an assay that detects NGAL (and/or one or more related markers), and reagents for performing an assay that detects one or more of BNP, NT-proBNP, and proBNP (and/or one or more related markers).

DETAILED DESCRIPTION OF THE INVENTION

The present invention relates to methods and compositions for diagnosis, prognosis, and determination of treatment regimens in subjects suffering from renal dysfunction, heart failure, and cardiorenal syndrome.

Congestive heart failure (CHF) is a fatal disease with a 5-year mortality rate that rivals the most deadly malignancies. For example, in the Framingham Heart Study, median survival after the onset of heart failure was 1.7 years in men and 3.2 years in women. Overall, 1-year and 5-year survival rates were 57% and 25% in men and 64% and 38% in women, respectively. Moreover, a person age 40 or older has a one-in-five lifetime chance of developing congestive heart failure. Moreover, the body relies on a coupling of renal function to cardiac function, a characteristic sometimes referred to as the "cardiorenal axis." While the precise pathophysiological mechanisms underlying this relationship between the heart and kidneys are still emerging, it has now become clear that the co-existence renal dysfunction and heart failure signals an extremely bad prognosis.

The appropriate treatments given to patients suffering from renal dysfunction and heart failure can be large and diverse. Unfortunately, many treatments given for various diseases may adversely affect the cardiorenal axis. For example, diuretics are often given to reduce the increased fluid load characteristic of heart failure, and non-steroidal anti-inflammatory drugs (NSAIDs) are often prescribed to elderly subjects. Each of these drugs increase the risk of damage to both the heart and kidneys.

The present invention provides methods and compositions that may be used to monitor the cardiorenal axis in an improved manner. By monitoring the ends of this axis using markers that provide an early indication that damage may follow, treatments may be balanced to provide benefit to the patient while at the same time preserving cardiorenal status. For example, treatments known to damage the heart and/or kidney may be temporarily removed in the face of a worsening cardiorenal syndrome status or worsening renal function. Alternatively, or in addition, palliative treatments may be selected and initiated in an attempt to improve the function of the heart or kidney, while observing the overall effect on the cardiorenal syndrome status of the patient.

The term "renal dysfunction" as used herein refers to a reduced level of kidney function, relative to normal, and is indicated by a serum or plasma creatinine level 1.4 mg/dL or greater, a creatinine clearance rate of 60 mL/min/1.73 m$^2$ or less, a serum or plasma cystatin C level of 1 mg/L or greater, or the presence of chronic kidney disease as defined by the National Kidney Foundation in "National Kidney Foundation. Kidney Disease Outcome Quality Initiative (K/DOQI) clinical practice guidelines for chronic kidney disease: evaluation, classification, and stratification," *Am. J. Kidney Dis.* 39(Suppl 1):S1-S266, 2002, which is hereby incorporated by reference in its entirety. Chronic kidney disease includes persistent kidney damage, as reflected by a glomerular filtration rate (GFR) of less than 60.0 mL/minute/1.73 m$^2$ of body-surface area for more than three months. Included are patients with end-stage renal disease, as defined by a GFR of less than 10.0 mL/minute/1.73 m$^2$. Because practical limitations exist in measuring GFR directly, especially in acutely ill patients, clinical variables may be used to estimate the GFR. See, e.g., Levey et al., "A more accurate method to estimate glomerular filtration rate from serum creatinine: a new prediction equation," *Ann. Intern. Med.* 130: 461-70, 1999, which is hereby incorporated by reference in its entirety.

Preferred subjects having renal dysfunction are those having severe renal dysfunction (defined herein as serum or plasma creatinine >2.5 mg/dL, serum or plasma cystatin C >2 mg/L, or creatinine clearance rates of <25 mL/minute/1.73 m$^2$), more preferred subjects have moderate renal dysfunction (defined herein as serum or serum or plasma creatinine of 1.9 to 2.5 mg/dL, serum or plasma cystatin C of 2 to 1.5 mg/L, or creatinine clearance rates of 25-30 mL/minute/1.73 m$^2$), and most preferred subjects have mild renal dysfunction (defined herein as serum or plasma creatinine of 1.4 to 2.25 mg/dL, serum or plasma cystatin C of 1 to 1.5 mg/L, or creatinine clearance rates of 30-60 mL/minute/1.73 m$^2$).

The term "risk of worsening renal function" as used herein refers to assignment of a particular prognosis—a likelihood that a subject will suffer, most preferably in the short term, from deterioration of one or more measures of kidney function selected from the group consisting of serum or plasma creatinine levels, creatinine clearance rates, serum or plasma cystatin C levels, chronic kidney disease stage (as defined by the National Kidney Foundation in "National Kidney Foundation. Kidney Disease Outcome Quality Initiative (K/DOQI) clinical practice guidelines for chronic kidney disease: evaluation, classification, and stratification," *Am. J. Kidney Dis.* 39(Suppl 1): S1-S266, 2002), stage of renal dysfunction, and glomerular filtration rate, or, in the extreme, will die (that is, a likelihood of mortality in the subject).

As described herein, the present invention relates in part to assigning a risk of worsening renal function based, at least in part, on the result of an assay that detects NGAL performed on a body fluid sample obtained from a subject. If the sample tested is obtained from the subject at a time t, the phrase "the short term" refers to a 7-day (168 hour) period measured from time t. Thus, the risk is a likelihood that the subject will suffer from deterioration of one or more of these measures of kidney function, or will die, in a window beginning at time t and ending 168 hours later. More preferably, the risk is a likelihood that the subject will suffer from deterioration of one or more of these measures of kidney function, or will die, in a 96 hour window beginning at time t, and most preferably the risk is a likelihood that the subject will suffer from deterioration of one or more of these measures of kidney function, or a likelihood that the subject will die, in a window of between 48 and 84 hours beginning at time t.

The term "deterioration" as used herein refers to a change in a parameter at a later time, relative to a measure of the same parameter earlier in the same subject, and is the opposite of "improvement." Thus, the terms "deterioration of serum or plasma creatinine levels" and "deterioration of serum or plasma cystatin C levels" as used herein refer to an increase in the creatinine or cystatin C assay result in a sample obtained from a subject at a time later than time t, relative to that measured in the subject at time t. Similarly, "deterioration of creatinine clearance rates" as used herein refers to a later decrease in creatinine clearance rate for the subject, relative to that measured at time t. "Deterioration in chronic kidney disease stage" as used herein refers to a later change to a higher stage in the subject, relative to that observed at time t. "Deterioration of stage of renal dysfunction" as used herein refers to a later change in the subject from mild to moderate or severe, or a change from moderate to severe, relative to the stage of renal dysfunction observed at time t. Finally, "deterioration of glomerular filtration rate" as used herein refers to a later decrease in GFR in the subject, relative to that observed at time t.

The term "monitoring cardiorenal syndrome" refers to observing a patient diagnosed with heart failure for changes in coordination between renal and cardiac functions as measured by a change in renal function, cardiac output function, or both. A "change in cardiorenal syndrome status" as used herein refers to assignment of a particular prognosis—the likelihood that a subject diagnosed with heart failure will suffer, most preferably in the short term, from a change (improvement or deterioration) of one or more measures of renal or cardiac output function, or, in the extreme, the likelihood that a subject diagnosed with heart failure will die (that is, a likelihood of mortality in the subject). As described herein, NGAL assays may be used to predict changes in renal function, the future onset of renal dysfunction, and/or worsening of renal function. Similarly, as described herein, assays for BNP and its related polypeptides may be used to predict changes in cardiac output function in heart failure. By combining these measurements, the skilled artisan can initiate or alter treatment of a subject in advance of the subject exhibiting outward clinical signs of deteriorating cardiorenal syndrome status.

The term "cardiac output function" as used herein refers to one or more characteristics of heart function that are affected in subjects diagnosed with heart failure. Such characteristics include one or more of: dyspnea (at rest or exertional), orthopnea, pulmonary edema, $SaO_2$ level, dizziness or syncope, chest pain, systolic blood pressure, hypoperfusion, edema, NYHA grade, compensation status (that is, a change from compensated to decompensated, or vice versa), ejection fraction, end-diastolic function, end-systolic function, ventricular filling, and flow across the mitral valve. These characteristics, and methods for their assessment, are well known in the art. See, e.g., *Harrison's Principles of Internal Medicine*, 16$^{th}$ ed., McGraw-Hill, 2005, pages 1361-1377, which is hereby incorporated by reference in its entirety. As discussed above, "deterioration" as used herein refers to a change in a parameter at a later time, relative to a measure of the same parameter earlier in the same subject. Thus, "deterioration in cardiac output function" refers to a change in one or more of these characteristics indicative of a clinical worsening of heart failure in a subject.

The term "marker" as used herein refers to proteins, polypeptides, glycoproteins, proteoglycans, lipids, lipoproteins, glycolipids, phospholipids, nucleic acids, carbohydrates, etc. or small molecules to be used as targets for screening test samples obtained from subjects. "Proteins or polypeptides" used as markers in the present invention are contemplated to include any fragments thereof, in particular, immunologically detectable fragments. Markers can also include clinical "scores" such as a pre-test probability assignment, a pulmonary hypertension "Daniel" score, an NIH stroke score, a Sepsis Score of Elebute and Stoner, a Duke Criteria for Infective Endocarditis, a Mannheim Peritonitis Index, an "Apache" score, etc.

The term "related marker" as used herein refers to one or more fragments of a particular marker or its biosynthetic parent that may be detected as a surrogate for the marker itself or as independent markers. For example, human BNP is derived by proteolysis of a 108 amino acid precursor molecule, referred to hereinafter as $BNP_{1-108}$. Mature BNP, or "the BNP natriuretic peptide," or "BNP-32" is a 32 amino acid molecule representing amino acids 77-108 of this precursor, which may be referred to as $BNP_{77-108}$. The remaining residues 1-76 are referred to hereinafter as $BNP_{1-76}$, and are also known as "NT-proBNP." Additionally, related markers may be the result of covalent modification of the parent marker, for example by oxidation of methionine residues, ubiquitination, cysteinylation, nitrosylation (e.g., containing nitrotyrosine residues), halogenation (e.g., containing chlorotyrosine and/or bromotyrosine residues), glycosylation, complex formation, differential splicing, etc. Preferred related markers are "immunologically detectable," meaning a fragment of a particular marker or its biosynthetic parent that comprises at least one epitope (antigenic site on the plypeptide to which an antibody binds) that is also present in the marker or its biosynthetic parent. Preferred immunologically detectable fragments comprise at least 8 contiguous residues of the marker or its biosynthetic parent.

The sequence of the 108 amino acid BNP precursor pro-BNP ($BNP_{1-108}$) is as follows, with mature BNP ($BNP_{77-108}$) underlined:

```
                                                      (SEQ ID NO: 1)
HPLGSPGSAS DLETSGLQEQ RNHLQGKLSE LQVEQTSLEP LQESPRPTGV    50

WKSREVATEG IRGHRKMVLY TLRAPRSPKM VQGSGCFGRK MDRISSSSGL   100

GCKVLRRH.                                               108
```

$BNP_{1-108}$ is synthesized as a larger precursor pre-pro-BNP having the following sequence (with the "pre" sequence shown in bold):

```
                                                      (SEQ ID NO: 2)
MDPQTAPSRA LLLLLFLHLA FLGGRSHPLG SPGSASDLET SGLQEQRNHL    50

QGKLSELQVE QTSLEPLQES PRPTGVWKSR EVATEGIRGH RKMVLYTLRA   100

PRSPKMVQGS GCFGRKMDRI SSSSGLGCKV LRRH.                  134
```

While mature BNP itself may be used as a marker in the present invention, the prepro-BNP, $BNP_{1-108}$ and $BNP_{1-76}$ molecules represent BNP-related markers that may be measured either as surrogates for mature BNP or as markers in and of themselves. In addition, one or more fragments of these molecules, including BNP-related polypeptides selected from the group consisting of $BNP_{77-106}$, $BNP_{79-106}$, $BNP_{76-107}$, $BNP_{69-108}$, $BNP_{79-108}$, $BNP_{80-108}$, $BNP_{81-108}$, $BNP_{83-108}$, $BNP_{39-86}$, $BNP_{53-85}$, $BNP_{66-98}$, $BNP_{30-103}$, $BNP_{11-107}$, $BNP_{9-106}$, and $BNP_{3-108}$, may also be present in circulation. In addition, natriuretic peptide fragments, including BNP fragments, may comprise one or more oxidizable methionines, the oxidation of which to methionine sulfoxide or methionine sulfone produces additional BNP-related markers. See, e.g., U.S. Pat. No. 10/419,059, filed Apr. 17, 2003, which is hereby incorporated by reference in its entirety including all tables, figures and claims. Moreover, assays may intentionally use proteolysis to generate fragments of a marker, which may then be measured. See, e.g., Goetze et al., "Quantification of pro-B-type natriuretic peptide and its products in human plasma by use of an analysis independent of precursor processing," *Clin. Chem.* 48: 1035-42, 2002. "Related markers" to each of the markers described herein may be identified and used in an analogous fashion to that described above for BNP.

Because production of marker fragments is an ongoing process that may be a function of, inter alia, the elapsed time between onset of an event triggering marker release into the tissues and the time the sample is obtained or analyzed; the elapsed time between sample acquisition and the time the sample is analyzed; the type of tissue sample at issue; the storage conditions; the quantity of proteolytic enzymes present; etc., it may be necessary to consider this degradation when both designing an assay for one or more markers, and when performing such an assay, in order to provide an accurate prognostic or diagnostic result. In addition, individual antibodies that distinguish amongst a plurality of marker fragments may be individually employed to separately detect the presence or amount of different fragments. The results of this individual detection may provide a more accurate prognostic or diagnostic result than detecting the plurality of fragments in a single assay. For example, different weighting factors may be applied to the various fragment measurements to provide a more accurate estimate of the amount of natriuretic peptide originally present in the sample.

The failure to consider the degradation fragments that may be present in a clinical sample may have serious consequences for the accuracy of any diagnostic or prognostic method. Consider for example a simple case, where a sandwich immunoassay is provided for BNP, and a significant amount (e.g., 50%) of the biologically active BNP that had been present has now been degraded into an inactive form. An immunoassay formulated with antibodies that bind a region common to the biologically active BNP and the inactive fragment(s) will overestimate the amount of biologically active BNP present in the sample by 2-fold, potentially resulting in a "false positive" result. Overestimation of the biologically active form(s) present in a sample may also have serious consequences for patient management. Considering the BNP example again, the BNP concentration may be used to determine if therapy is effective (e.g., by monitoring BNP to see if an elevated level is returning to normal upon treatment). The same "false positive" BNP result discussed above may lead the physician to continue, increase, or modify treatment because of the false impression that current therapy is ineffective.

Likewise, it may be necessary to consider the complex state of one or more markers described herein. For example, troponin exists in muscle mainly as a "ternary complex" comprising three troponin polypeptides (T, I and C). But troponin I and troponin T circulate in the blood in forms other than the I/T/C ternery complex. Rather, each of (i) free cardiac-specific troponin I, (ii) binary complexes (e.g., troponin I/C complex), and (iii) ternary complexes all circulate in the blood. Furthermore, the "complex state" of troponin I and T may change over time in a patient, e.g., due to binding of free troponin polypeptides to other circulating troponin polypeptides. Immunoassays that fail to consider the "complex state" of troponin may not detect all of the cardiac-specific isoform of interest.

Preferred assays are "configured to detect" a particular marker. That an assay is "configured to detect" a marker means that an assay can generate a detectable signal indicative of the presence or amount of a physiologically relevant concentration of a particular marker of interest. Such an assay may, but need not, specifically detect a particular marker (i.e., detect a marker but not some or all related markers). Because an antibody epitope is on the order of 8 amino acids, an immunoassay will detect other polypeptides (e.g., related markers) so long as the other polypeptides contain the epitope(s) necessary to bind to the antibody used in the assay. Such other polypeptides are referred to as being "immunologically detectable" in the assay, and would include various isoforms (e.g., splice variants). In the case of a sandwich immunoassay, related markers must contain at least the two epitopes bound by the antibody used in the assay in order to be detected. Taking $BNP_{79-108}$ as an example, an assay configured to detect this marker may also detect $BNP_{77-108}$ or $BNP_{1-108}$, as such molecules may also contain the epitope(s) present on $BNP_{79-108}$ to which the assay antibody binds. However, such assays may also be configured to be "sensitive" to loss of a particular epitope, e.g., at the amino and/or carboxyl terminus of a particular polypeptide of interest as described in US2005/0148024, which is hereby incorporated by reference in its entirety. As described therein, an antibody may be selected that would bind to the amino terminus of $BNP_{79-108}$ such that it does not bind to $BNP_{77-108}$. Similar assays that bind $BNP_{3-108}$ and that are "sensitive" to loss of a particular epitipe, e.g., at the amino and/or carboxyl terminus are also described therein.

The methods described hereinafter utilize assays that detect BNP, NGAL, and/or their related markers. Such markers are referred to herein as being "subject-derived." The term "subject-derived marker" as used herein refers to protein, polypeptide, phospholipid, nucleic acid, prion, glycoprotein, proteoglycan, glycolipid, lipid, lipoprotein, carbohydrate, or small molecule markers that are expressed or produced by one or more cells of the subject. Additional markers may be used that are derived not from the subject, but rather that are expressed by pathogenic or infectious organisms that are correlated with a particular disease. Such markers are preferably protein, polypeptide, phospholipid, nucleic acid, prion, or small molecule markers that identify the infectious diseases described above. These subject-derived markers are measured in a test sample, most preferably a body fluid sample.

The term "test sample" as used herein refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

As used herein, a "plurality" as used herein refers to at least two. Preferably, a plurality refers to at least 3, more preferably at least 5, even more preferably at least 10, even more preferably at least 15, and most preferably at least 20. In particularly preferred embodiments, a plurality is a large number, i.e., at least 100.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are "patients," i.e., living humans that are receiving medical care for a disease or condition. This includes persons with no defined illness who are being investigated for signs of pathology.

The term "diagnosis" as used herein refers to methods by which the skilled artisan can estimate and/or determine whether or not a patient is suffering from a given disease or condition. The skilled artisan often makes a diagnosis on the basis of one or more diagnostic indicators, i.e., a marker, the presence, absence, amount, or change in amount of which is indicative of the presence, severity, or absence of the condition. The term "diagnosis" does not refer to the ability to determine the presence or absence of a particular disease with 100% accuracy, or even that a given course or outcome is more likely to occur than not. Instead, the skilled artisan will understand that the term "diagnosis" refers to an increased probability that a certain disease is present in the subject.

Similarly, a prognosis is often determined by examining one or more "prognostic indicators." These are markers, the presence or amount of which in a patient (or a sample obtained from the patient) signal a probability that a given course or outcome will occur. For example, when one or more prognostic indicators reach a sufficiently high level in samples obtained from such patients, the level may signal that the patient is at an increased probability for experiencing morbidity or mortality in comparison to a similar patient exhibiting a lower marker level. A level or a change in level of a prognostic indicator, which in turn is associated with an increased probability of morbidity or death, is referred to as being "associated with an increased predisposition to an adverse outcome" in a patient.

The term "correlating" or "relating" as used herein in reference to the use of markers, refers to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a profile of marker levels are correlated to a global probability or a particular outcome using ROC curves.

In certain embodiments, the methods described herein comprise the comparison of an assay result to a corresponding baseline result. The term "baseline result" as used herein refers to an assay value that is used as a comparison value (that is, to which a test result is compared). In practical terms, this means that a marker is measured in a sample from a subject, and the result is compared to the baseline result. A value above the baseline indicates a first likelihood of a diagnosis or prognosis, and a value below the baseline indicates a second likelihood of a diagnosis or prognosis.

In certain embodiments, a baseline for NGAL (and/or one or more markers related thereto) is established, and an NGAL assay result is established by performing an assay method that detects NGAL on a sample from a patient. That NGAL result is compared to the NGAL baseline result, and a value above the baseline indicates worsening renal function, relative to a value below the baseline. Similarly, a value below the baseline indicates improved renal function, relative to a value above the baseline.

In certain embodiments, a baseline for NGAL (and/or one or more markers related thereto) is established, and an NGAL assay result is established by performing an assay method that detects NGAL on a sample from a patient. That NGAL result is compared to the NGAL baseline result, and a value above the baseline indicates an increased mortality risk, relative to a value below the baseline. Similarly, a value below the baseline indicates a decrease mortality risk, relative to a value above the baseline.

In other embodiments, a baseline for NGAL (and/or one or more markers related thereto) is established, and an NGAL assay result is established by performing an assay method that detects NGAL on a sample from a patient. That NGAL result is compared to the NGAL baseline result, and a value above the baseline indicates worsening renal function, relative to a value below the baseline. Similarly, a value below the baseline indicates improved renal function, relative to a value above the baseline.

In still other embodiments, a baseline for NGAL (and/or one or more markers related thereto) is established, and an NGAL assay result is established by performing an assay method that detects NGAL on a sample from a patient. That NGAL result is compared to the NGAL baseline result, and a value above the baseline indicates worsening cardiorenal syndrome status, relative to a value below the baseline. Similarly, a value below the baseline indicates improved cardiorenal syndrome status, relative to a value above the baseline.

In yet other embodiments, a natriuretic peptide baseline (for BNP and/or one or more markers related thereto) is established, and a natriuretic peptide assay result is established by performing an assay method that detects BNP (and/or one or more markers related thereto) on a sample from a patient. That natriuretic peptide assay result is compared to the natriuretic peptide baseline result, and a value above the baseline indicates worsening cardiorenal syndrome status, relative to a value below the baseline. Similarly, a value below the baseline indicates improved cardiorenal syndrome status, relative to a value above the baseline.

A baseline can be selected in a number of manners well known to those of skill in the art. For example, data for a marker or markers (e.g., concentration in a body fluid, such as urine, blood, serum, or plasma) may be obtained from a population of subjects. The population of subjects is divided into at least two subpopulations. The first subpopulation includes those subjects who have been confirmed as having a disease, outcome, or, more generally, being in a first condition state. For example, this first subpopulation of patients may be those diagnosed with heart failure, and that suffered from a worsening of renal function. For convenience, subjects in this first subpopulation will be referred to as "diseased," although in fact, this subpopulation is actually selected for the presence of a particular characteristic of interest. The second subpopulation of subjects is formed from the subjects that do not fall within the first subpopulation. Subjects in this second set will hereinafter be referred to as "non-diseased."

A baseline result may then be selected to distinguish between the diseased and non-diseased subpopulation with an acceptable specificity and sensitivity. Changing the baseline merely trades off between the number of false positives and the number of false negatives resulting from the use of the particular marker under study. The effectiveness of a test having such an overlap is often expressed using a ROC (Receiver Operating Characteristic) curve. ROC curves are well known to those skilled in the art. The horizontal axis of the ROC curve represents (1−specificity), which increases with the rate of false positives. The vertical axis of the curve represents sensitivity, which increases with the rate of true positives. Thus, for a particular cutoff selected, the value of (1−specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In an alternative, an individual subject may provide their own baseline, in that a temporal change is used to indicate a particular diagnosis or prognosis. For example, one or more markers may be determined at an initial time to provide one or more baseline results, and then again at a later time, and the change (or lack thereof) in the marker level(s) over time determined. In such embodiments, an increase in the marker from the initial time to the second time may be indicative of a particular prognosis, of a particular diagnosis, etc. Likewise, a decrease in the marker from the initial time to the second time may be indicative of a particular prognosis, of a particular diagnosis, etc. In such an embodiment, a plurality of markers need not change in concert with one another. Temporal changes in one or more markers may also be used together with single time point marker levels compared to a population-based baseline.

As discussed herein, the measurement of the level of a single marker may be augmented by additional markers. For example, other markers related to blood pressure regulation, including other natriuretic peptides and/or their related markers may be used together with, or separately from, BNP and/or its related markers. Suitable assays include, but are not limited to, assays that detect ANP, proANP, NT-proANP, CNP, Kininogen, CGRP II, urotensin II, BNP, NT-proBNP, proBNP, calcitonin gene related peptide, arg-Vasopressin, Endothelin-1 (and/or Big ET-1), Endothelin-2 (and/or Big ET-2), Endothelin-3 (and/or Big ET-3), procalcitonin, calcyphosine, adrenomedullin, aldosterone, angiotensin 1 (and/or angiotensinogen 1), angiotensin 2 (and/or angiotensinogen 2), angiotensin 3 (and/or angiotensinogen 3), Bradykinin, Tachykinin-3, calcitonin, Renin, Urodilatin, and Ghrelin, and/or one or more markers related thereto.

Other markers of renal function may also be used in the methods described herein. These include serum creatinine levels, creatinine clearance rates, cystatin C levels, and glomerular filtration rates.

In addition, subjects suffering from heart failure and renal dysfunction are often at increased risk for cardiovascular diseases, including potentially fatal arrhythmias and acute coronary syndromes. Thus, various subject-derived markers of cardiovascular risk may be included together with NGAL (and/or its related markers) and, where appropriate BNP (and/or its related markers). Suitable subject-derived markers include markers related to myocardial injury, markers related to coagulation and hemostasis, and markers related to inflammation. In addition, because of injury to pulmonary tissues occurring in heart failure, various markers related to pulmonary injury may also be included. Exemplary subject-derived markers are provided in the following table:

| Marker | Classification |
| --- | --- |
| Neutrophil elastase | Pulmonary injury |
| KL-6 | Pulmonary injury |
| LAMP 3 | Pulmonary injury |
| LAMP3 | Pulmonary injury |
| Lung Surfactant protein A | Pulmonary injury |
| Lung Surfactant protein B | Pulmonary injury |
| Lung Surfactant protein C | Pulmonary injury |
| Lung Surfactant protein D | Pulmonary injury |
| phospholipase D | Pulmonary injury |
| PLA2G5 | Pulmonary injury |
| SFTPC | Pulmonary injury |
| Myoglobin | Tissue injury |
| E-selectin | Tissue injury |
| VEGF | Tissue injury |
| EG-VEGF | Tissue injury |
| Troponin I and complexes | Myocardial injury |
| Troponin T and complexes | Myocardial injury |
| Annexin V | Myocardial injury |
| B-enolase | Myocardial injury |
| CK-MB | Myocardial injury |
| Glycogen phosphorylase-BB | Myocardial injury |
| Heart type fatty acid binding protein | Myocardial injury |
| Phosphoglyceric acid mutase | Myocardial injury |
| S-100ao | Myocardial injury |
| Plasmin | Coagulation and hemostasis |
| Thrombin | Coagulation and hemostasis |
| Antithrombin-III | Coagulation and hemostasis |
| Fibrinogen | Coagulation and hemostasis |
| von Willebrand factor | Coagulation and hemostasis |
| D-dimer | Coagulation and hemostasis |
| PAI-1 | Coagulation and hemostasis |
| Protein C | Coagulation and hemostasis |
| Soluble Endothelial Protein C Receptor (EPCR) | Coagulation and hemostasis |
| TAFI | Coagulation and hemostasis |
| Fibrinopeptide A | Coagulation and hemostasis |
| Plasmin alpha 2 antiplasmin complex | Coagulation and hemostasis |
| Platelet factor 4 | Coagulation and hemostasis |
| Platelet-derived growth factor | Coagulation and hemostasis |
| P-selectin | Coagulation and hemostasis |
| Prothrombin fragment 1 + 2 | Coagulation and hemostasis |
| B-thromboglobulin | Coagulation and hemostasis |
| Thrombin antithrombin III complex | Coagulation and hemostasis |
| Thrombomodulin | Coagulation and hemostasis |
| Thrombus Precursor Protein | Coagulation and hemostasis |
| Tissue factor | Coagulation and hemostasis |
| Tissue factor pathway inhibitor-α | Coagulation and hemostasis |
| Tissue factor pathway inhibitor-β | Coagulation and hemostasis |
| APRIL (TNF ligand superfamily member 13) | Inflammatory |
| CD27 (TNFRSF7) | Inflammatory |
| Complement C3a | Inflammatory |
| CCL-5 (RANTES) | Inflammatory |
| CCL-8 (MCP-2) | Inflammatory |
| CCL-16 | Inflammatory |
| CCL-19 (macrophage inflammatory protein-3β) | Inflammatory |
| CCL-20 (MIP-3α) | Inflammatory |
| CCL-23 (MIP-3) | Inflammatory |
| CXCL-5 (small inducible cytokine B5) | Inflammatory |
| CXCL-9 (small inducible cytokine B9) | Inflammatory |
| CXCL-13 (small inducible cytokine B13) | Inflammatory |
| CXCL-16 (small inducible cytokine B16) | Inflammatory |
| DPP-II (dipeptidyl peptidase II) | Inflammatory |
| DPP-IV (dipeptidyl peptidase IV) | Inflammatory |
| Glutathione S Transferase | Inflammatory |
| HIF 1 ALPHA | Inflammatory |
| IL-25 | Inflammatory |
| IL-23 | Inflammatory |
| IL-22 | Inflammatory |
| IL-18 | Inflammatory |
| IL-13 | Inflammatory |
| IL-12 | Inflammatory |
| IL-10 | Inflammatory |
| IL-1-Beta | Inflammatory |
| IL-1ra | Inflammatory |
| IL-4 | Inflammatory |
| IL-6 | Inflammatory |
| IL-8 | Inflammatory |
| Lysophosphatidic acid | Inflammatory |
| MDA-modified LDL | Inflammatory |
| Human neutrophil elastase | Inflammatory |
| C-reactive protein | Inflammatory |
| Insulin-like growth factor | Inflammatory |
| Inducible nitric oxide synthase | Inflammatory |
| Intracellular adhesion molecule | Inflammatory |
| Lactate dehydrogenase | Inflammatory |
| MCP-1 | Inflammatory |
| MMP-1 | Inflammatory |
| MMP-2 | Inflammatory |
| MMP-3 | Inflammatory |
| MMP-7 | Inflammatory |
| MMP-9 | Inflammatory |
| TIMP-1 | Inflammatory |
| TIMP-2 | Inflammatory |
| TIMP-3 | Inflammatory |
| NGAL | Inflammatory |
| n-acetyl aspartate | Inflammatory |
| PTEN | Inflammatory |
| Phospholipase A2 | Inflammatory |
| TNF Receptor Superfamily Member 1A | Inflammatory |
| TNFRSF3 (lymphotoxin β receptor) | Inflammatory |
| Transforming growth factor beta | Inflammatory |
| TREM-1 | Inflammatory |
| TREM-1sv | Inflammatory |
| TL-1 (TNF ligand related molecule-1) | Inflammatory |
| TL-1a | Inflammatory |
| Tumor necrosis factor alpha | Inflammatory |
| Vascular cell adhesion molecule | Inflammatory |
| Vascular endothelial growth factor | Inflammatory |
| cystatin C | Inflammatory |
| substance P | Inflammatory |
| Myeloperoxidase (MPO) | Inflammatory |
| macrophage inhibitory factor | Inflammatory |
| Fibronectin | Inflammatory |
| cardiotrophin 1 | Inflammatory |
| Haptoglobin | Inflammatory |
| PAPPA | Inflammatory |
| S-CD40 ligand | Inflammatory |
| HMG-1 (or HMGB1) | Inflammatory |
| IL-2 | Inflammatory |
| IL-4 | Inflammatory |
| IL-11 | Inflammatory |
| IL-13 | Inflammatory |
| IL-18 | Inflammatory |
| Eosinophil cationic protein | Inflammatory |
| Mast cell tryptase | Inflammatory |
| VCAM | Inflammatory |
| sICAM-1 | Inflammatory |
| TNFα | Inflammatory |
| Osteoprotegerin | Inflammatory |

-continued

| Marker | Classification |
| --- | --- |
| Prostaglandin D-synthase | Inflammatory |
| Prostaglandin E2 | Inflammatory |
| RANK ligand | Inflammatory |
| RANK (TNFRSF11A) | Inflammatory |
| HSP-60 | Inflammatory |
| Serum Amyloid A | Inflammatory |
| s-iL 18 receptor | Inflammatory |
| S-iL-1 receptor | Inflammatory |
| s-TNFR1 (P55) | Inflammatory |
| s-TNFR2 (P75) | Inflammatory |
| sTLR-1 (soluble toll-like receptor-1) | Inflammatory |
| sTLR-2 | Inflammatory |
| sTLR-4 | Inflammatory |
| TGF-beta | Inflammatory |
| MMP-11 | Inflammatory |
| Beta NGF | Inflammatory |
| CD44 | Inflammatory |
| EGF | Inflammatory |
| E-selectin | Inflammatory |
| Fibronectin | Inflammatory |
| RAGE | Inflammatory |

Various clinical variables may also be utilized as variables in the methods described herein. Examples of such variables include urine output levels, age, the presence or absence of one or more cardiovascular risk factors such as diabetes, hypertension, smoking status, etc. This list is not meant to be limiting.

Suitable methods for combining markers into a single composite value that may be used as if it is a single marker are described in detail in U.S. Provisional Patent Application No. 60/436,392 filed Dec. 24, 2002, PCT application US03/41426 filed Dec. 23, 2003, U.S. patent application Ser. No. 10/331,127 filed Dec. 27, 2002, and PCT application No. US03/41453, each of which is hereby incorporated by reference in its entirety, including all tables, figures, and claims. In an alternative, NGAL assay results, natriuretic peptide assay results, and other optional test results may be used in an "n-of-m" type of approach. Using a two marker example of such methods, when either marker above its corresponding baseline value may signal an increased risk of an adverse outcome, or a worsening in cardiorenal syndrome status (in n-of-m terms, this is a "1-of-2" result). If both are above the corresponding baselines (a "2-of-2" result), an even greater worsening in cardiorenal syndrome status may be indicated.

The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations. For any particular marker, a distribution of marker levels for subjects with and without a "disease" will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create an ROC curve. For example, results of a test on "disease" samples might be ranked according to degree (say 1=low, 2=normal, and 3=high). This ranking can be correlated to results in the "normal" population, and a ROC curve created. These methods are well known in the art. See, e.g., Hanley et al., *Radiology* 143: 29-36 (1982).

Measures of test accuracy may also be obtained as described in Fischer et al., *Intensive Care Med.* 29: 1043-51, 2003, and used to determine the effectiveness of a given marker or panel of markers. These measures include sensitivity and specificity, predictive values, likelihood ratios, diagnostic odds ratios, and ROC curve areas. As discussed above, preferred tests and assays exhibit one or more of the following results on these various measures.

Preferably, a baseline is chosen to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. An odds ratio of at least about 1.25 or about 0.8 or less can provide acceptable performance. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/−5% of a given measurement.

Numerous methods and devices are well known to the skilled artisan for the detection and analysis of the markers of the instant invention. With regard to polypeptides or proteins in patient test samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman Access, Abbott AxSym, Roche ElecSys, Dade Behring Stratus systems are among the immunoassay analyzers that are capable of performing the immunoassays taught herein.

Preferably the markers are analyzed using an immunoassay, and most preferably sandwich immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Biological assays such as immunoassays require methods for detection, and one of the most common methods for quantitation of results is to conjugate an enzyme, fluorophore or other molecule to form an antibody-label conjugate. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.). Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of *Immunoassay*, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001. The antibodies could be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot. When multiple assays are being performed, a plurality of separately addressable locations, each corresponding to a different marker and comprising antibodies that bind the appropriate marker, can be provided on a single solid support. The term "discrete" as used herein refers to areas of a surface that are non-contiguous. That is, two areas are discrete from one another if a border that is not part of either area completely surrounds each of the two areas. The term "independently addressable" as used herein refers to discrete areas of a surface from which a specific signal may be obtained.

For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses perform simultaneous assays of a plurality of markers using a single test device. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

Preferred assay devices of the present invention will comprise, for one or more assays, a first antibody conjugated to a solid phase and a second antibody conjugated to a signal development element. Such assay devices are configured to perform a sandwich immunoassay for one or more analytes. These assay devices will preferably further comprise a sample application zone, and a flow path from the sample application zone to a second device region comprising the first antibody conjugated to a solid phase.

Flow of a sample in an assay device along the flow path may be driven passively (e.g., by capillary, hydrostatic, or other forces that do not require further manipulation of the device once sample is applied), actively (e.g., by application of force generated via mechanical pumps, electroosmotic pumps, centrifugal force, increased air pressure, etc.), or by a combination of active and passive driving forces. Most preferably, sample applied to the sample application zone will contact both a first antibody conjugated to a solid phase and a second antibody conjugated to a signal development element along the flow path (sandwich assay format). Additional elements, such as filters to separate plasma or serum from blood, mixing chambers, etc., may be included as required by the artisan. Exemplary devices are described in Chapter 41, entitled "Near Patient Tests: Triage® Cardiac System," in *The Immunoassay Handbook*, $2^{nd}$ ed., David Wild, ed., Nature Publishing Group, 2001, which is hereby incorporated by reference in its entirety.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

In another embodiment, the present invention provides a kit for the analysis of markers. Such a kit preferably comprises devises and reagents for the analysis of at least one test sample and instructions for performing the assay(s) of interest. Optionally the kits may contain one or more means for using information obtained from immunoassays performed for a marker panel to rule in or out certain diagnoses or prognoses. Other measurement strategies applicable to the methods described herein include chromatography (e.g., HPLC), mass spectrometry, receptor-based assays, and combinations of the foregoing.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, $3^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

Preferably, an antibody is selected that specifically binds a marker of interest. The term "specifically binds" is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ $M^{-1}$. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{11}$ $M^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c = K(n-r)$:

where
r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1 \times 10^{-6}$ moles/liter, is more preferably at least about $1 \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The generation and selection of antibodies may be accomplished several ways. For example, one way is to purify polypeptides of interest or to synthesize the polypeptides of interest using, e.g., solid phase peptide synthesis methods well known in the art. See, e.g., Guide to Protein Purification, Murray P. Deutcher, ed., *Meth. Enzymol. Vol* 182 (1990); Solid Phase Peptide Synthesis, Greg B. Fields ed., *Meth. Enzymol. Vol* 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be injected, for example, into mice or rabbits, to generate polyclonal or monoclonal antibodies. One skilled in the art will recognize that many procedures are available for the production of antibodies, for example, as described in *Antibodies, A Laboratory Manual*, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (*Antibody Engineering: A Practical Approach*, Borrebaeck, C., ed., 1995, Oxford University Press, Oxford; *J. Immunol.* 149, 3914-3920 (1992)).

In addition, numerous publications have reported the use of phage display technology to produce and screen libraries of polypeptides for binding to a selected target. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

EXAMPLES

The following examples serve to illustrate the present invention. These examples are in no way intended to limit the scope of the invention.

Example 1

Biochemical Analyses

Markers were measured using standard immunoassay techniques. These techniques involve the use of antibodies to specifically bind the analyte(s) of interest. Immunoassays were performed using TECAN Genesis RSP 200/8 or Perkin Elmer Minitrak Workstations, or using microfluidic devices manufactured at Biosite Incorporated essentially as described in WO98/43739, WO98/08606, WO98/21563, and WO93/24231. Analytes may be measured using a sandwich immunoassay or using a competitive immunoassay as appropriate, depending on the characteristics and concentration range of the analyte of interest.

The assays were calibrated using purified proteins (that is either the same as or related to the selected analyte, and that can be detected in the assay) diluted gravimetrically into EDTA plasma treated in the same manner as the sample population specimens. Endogenous levels of the analyte present in the plasma prior to addition of the purified marker protein was measured and taken into account in assigning the marker values in the calibrators. When necessary to reduce endogenous levels in the calibrators, the endogenous analyte was stripped from the plasma using standard immunoaffinity methods. Calibrators were assayed in the same manner as the sample population specimens, and the resulting data used to construct a "dose-response" curve (assay signal as a function of analyte concentration), which may be used to determine analyte concentrations from assay signals obtained from subject specimens.

Individual assays were configured to bind the following markers, and results are reported in the following examples using the following units: BNP—pg/mL; NGAL—ng/mL; cystatin C—µg/mL.

Example 2

Microtiter Plate-Based Biochemical Analyses

For the sandwich immunoassay in microtiter plates, a monoclonal antibody directed against a selected analyte was biotinylated using N-hydroxysuccinimide biotin (NHS-biotin) at a ratio of about 5 NHS-biotin moieties per antibody. The antibody-biotin conjugate was then added to wells of a standard avidin 384 well microtiter plate, and antibody conjugate not bound to the plate was removed. This formed the "anti-marker" in the microtiter plate. Another monoclonal antibody directed against the same analyte was conjugated to alkaline phosphatase, for example using succinimidyl 4-[N-maleimidomethyl]-cyclohexane-1-carboxylate (SMCC) and N-succinimidyl 3-[2-pyridyldithio]propionate (SPDP) (Pierce, Rockford, Ill.).

Biotinylated antibodies were pipetted into microtiter plate wells previously coated with avidin and incubated for 60 min. The solution containing unbound antibody was removed, and the wells washed with a wash buffer, consisting of 20 mM borate (pH 7.42) containing 150 mM NaCl, 0.1% sodium azide, and 0.02% Tween-20. The plasma samples (10 µL) containing added HAMA inhibitors were pipeted into the microtiter plate wells, and incubated for 60 min. The sample was then removed and the wells washed with a wash buffer. The antibody-alkaline phosphatase conjugate was then added to the wells and incubated for an additional 60 min, after which time, the antibody conjugate was removed and the wells washed with a wash buffer. A substrate, (AttoPhos®, Promega, Madison, Wis.) was added to the wells, and the rate of formation of the fluorescent product is related to the concentration of the analyte in the sample tested.

Example 3

Microfluidic Device-Based Biochemical Analyses

Immunoassays were performed using microfluidic devices essentially as described in Chapter 41, entitled "Near Patient Tests: Triage® Cardiac System," in *The Immunoassay Handbook*, 2nd ed., David Wild, ed., Nature Publishing Group, 2001.

For sandwich immunoassays, a plasma sample was added to the microfluidic device that contains all the necessary assay reagents, including HAMA inhibitors, in dried form. The plasma passed through a filter to remove particulate matter. Plasma entered a "reaction chamber" by capillary action. This reaction chamber contained fluorescent latex particle-antibody conjugates (hereafter called FETL-antibody conjugates) appropriate to an analyte of interest, and may contain FETL-antibody conjugates to several selected analytes. The FETL-antibody conjugates dissolved into the plasma to form a reaction mixture, which was held in the reaction chamber for an incubation period (about a minute) to allow the analyte(s) of interest in the plasma to bind to the antibodies. After the incubation period, the reaction mixture moved down the detection lane by capillary action. Antibodies to the analyte(s) of interest were immobilized in discrete capture zones on the surface of a "detection lane." Analyte/antibody-FETL complexes formed in the reaction chamber were captured on an appropriate detection zone to form a sandwich complex, while unbound FETL-antibody conjugates were washed from the detection lane into a waste chamber by excess plasma. The amount of analyte/antibody-FETL complex bound on a capture zone was quantified with a fluorometer (Triage® Meter-Plus, Biosite Incorporated) and was related to the amount of the selected analyte in the plasma specimen.

Example 4

Assigning a Risk of an Adverse Outcome to a Subject Suffering from Heart Failure Samples were obtained from individuals presenting to the emergency department of a hospital for symptoms of congestive heart failure and that were subsequently treated for congestive heart failure, either in the emergency department or as an inpatient following admission to the hospital. Exclusion criteria were: less than 18 years of age, current MI or ACS with ST elevation of 1 mm or greater, renal failure requiring dialysis, hemodialysis within the last month, or a baseline BNP of 100 pg/mL or less. 90 day follow-up was by telephone, chart review, or mail.

From this population, individuals were selected such that 50 individuals fell into the following two possible groups: a serum creatinine ("sCr") at presentation of <1.6 mg/dL, and a serum creatinine ≧1.6 mg/dL. Possible outcomes examined were mortality within 90 days; an unplanned visit to the hospital for CHF or other cardiac event within 90 days (referred to collectively below as a "Cardiac Event"); an unplanned visit for a non-cardiac event within 90 days; or no such event within 90 days.

The following markers were measured in EDTA plasma samples: cystatin C, NGAL, and BNP. Reported values are cystatin C: μg/mL; NGAL: ng/mL; and BNP: pg/mL. The following are the descriptive statistics obtained. In these tables, the "event" group represents individuals experiencing mortality or an unplanned visit to the hospital for a Cardiac Event, in each case within 90 days.

| | sCr < 1.6, Event | | | | sCr ≧ 1.6, Event | | |
|---|---|---|---|---|---|---|---|
| n | CYSC 15 | NGAL 15 | BNP 15 | n | CYSC 15 | NGAL 15 | BNP 15 |
| Median | 1.29 | 94 | 370 | Median | 2.17 | 148 | 879 |
| Mean | 1.45 | 103 | 546 | Mean | 2.42 | 212 | 1328 |
| Min | 0.90 | 0 | 78 | Min | 1.088 | 0 | 113 |
| Max | 2.39 | 313 | 2226 | Max | 3.48 | 1233 | 4369 |
| Stdev | 0.40 | 75 | 549 | Stdev | 0.80 | 292 | 1252 |
| | sCr < 1.6, No Event | | | | sCr ≧ 1.6, No Event | | |
| n | CYSC 14 | NGAL 14 | BNP 14 | n | CYSC 14 | NGAL 14 | BNP 14 |
| Median | 1.25 | 69 | 281 | Median | 2.30 | 121 | 680 |
| Mean | 1.44 | 93 | 356 | Mean | 2.18 | 136 | 612 |
| Min | 0.76 | 0 | 78 | Min | 0.95 | 0 | 73 |
| Max | 3.09 | 473 | 1386 | Max | 3.32 | 333 | 1504 |
| Stdev | 0.70 | 123 | 316 | Stdev | 0.84 | 93 | 433 |
| | Any sCr, Event | | | | Any sCr, No Event | | |
| n | CYSC 30 | NGAL 30 | BNP 30 | n | CYSC 28 | NGAL 28 | BNP 28 |
| Median | 1.72 | 127 | 520 | Median | 1.46 | 99 | 328 |
| Mean | 1.93 | 158 | 937 | Mean | 1.81 | 114 | 484 |
| Min | 0.90 | 0 | 78 | Min | 0.76 | 0 | 73 |
| Max | 3.48 | 1233 | 4369 | Max | 3.32 | 473 | 1504 |
| Stdev | 0.79 | 217 | 1030 | Stdev | 0.85 | 109 | 394 |
| | sCr < 1.6, 90 d mortality | | | | sCr ≧ 1.6, 90 d mortality | | |
| n | CYSC 3 | NGAL 3 | BNP 3 | n | CYSC 4 | NGAL 4 | BNP 4 |
| Median | 1.70 | 176 | 519 | Median | 2.38 | 111 | 902 |
| Mean | 1.79 | 208 | 1027 | Mean | 2.37 | 114 | 1119 |
| Min | 1.29 | 136 | 337 | Min | 1.74 | 0 | 238 |
| Max | 2.39 | 313 | 2226 | Max | 2.98 | 232 | 2434 |
| Stdev | 0.56 | 93 | 1042 | Stdev | 0.59 | 131 | 963 |
| | Any sCr, 90 d mortality | | | | | | |
| n | CYSC 7 | NGAL 7 | BNP 7 | | | | |
| Median | 2.01 | 176 | 599 | | | | |
| Mean | 2.12 | 154 | 1080 | | | | |
| Min | 1.29 | 0 | 238 | | | | |
| Max | 2.98 | 313 | 2434 | | | | |
| Stdev | 0.61 | 119 | 910 | | | | |

ROC analysis was performed to determine the ability of these markers to predict outcome, as shown in the following tables. In each case, the "diseased" group refers to those suffering from mortality or a Cardiac Event (as indicated in the table), and "nondiseased" refers to the no event group. "Sense" indicates whether the marker is increasing or decreasing with "disease." P values were calculated using a one-sample Z test.

| | Mortality | | | Cardiac Event | | |
|---|---|---|---|---|---|---|
| sCR | <1.6 | ≧1.6 | Any | <1.6 | ≧1.6 | any |
| | Cystatin C | | | | | |
| ROC Area | 0.762 | 0.571 | 0.658 | 0.548 | 0.623 | 0.543 |
| N(diseased) | 14 | 14 | 28 | 14 | 14 | 28 |

-continued

| sCR | Mortality | | | Cardiac Event | | |
|---|---|---|---|---|---|---|
| | <1.6 | ≧1.6 | Any | <1.6 | ≧1.6 | any |
| N(nondiseased) | 3 | 4 | 7 | 12 | 11 | 23 |
| p value | 0.018 | 0.306 | 0.040 | 0.340 | 0.145 | 0.298 |
| Sense | Increasing | Increasing | Increasing | Increasing | Increasing | Increasing |
| | | | NGAL | | | |
| ROC Area | 0.881 | 0.571 | 0.628 | 0.530 | 0.643 | 0.557 |
| N(diseased) | 14 | 14 | 28 | 14 | 14 | 28 |
| N(nondiseased) | 3 | 4 | 7 | 12 | 11 | 23 |
| p value | <0.001 | 0.356 | 0.172 | 0.401 | 0.103 | 0.242 |
| Sense | Increasing | Increasing | Increasing | Increasing | Increasing | Increasing |
| | | | BNP | | | |
| ROC Area | 0.857 | 0.661 | 0.730 | 0.554 | 0.656 | 0.590 |
| N(diseased) | 14 | 14 | 28 | 14 | 14 | 28 |
| N(nondiseased) | 3 | 4 | 7 | 12 | 11 | 23 |
| p value | <0.001 | 0.174 | 0.014 | 0.330 | 0.090 | 0.135 |
| Sense | Increasing | Increasing | Increasing | Increasing | Increasing | Increasing |

These results indicate that cystatin C, NGAL, and BNP are each significant predictors of mortality, particularly in combination with a low initial serum creatinine level.

Using this data, odds ratios were calculated for the low serum creatine group, using the median measured level of each marker as a threshold:

| Marker | Odds ratio for mortality or cardiac event |
|---|---|
| Cystatin C | 1.5 |
| NGAL | 1.5 |
| BNP | 2.7 |
| Any one marker elevated | 4.9 |

Dividing the high serum creatinine group into tertiles, odds ratios were calculated comparing the first tertile to the third tertile:

| Marker | Odds ratio for mortality or cardiac event |
|---|---|
| Cystatin C | 2.3 |
| NGAL | 3.5 |
| BNP | 2.3 |
| Any one marker in $3^{rd}$ tertile | 3.7 |

These results demonstrate that each marker can be used to assign a relative risk of an adverse outcome to individuals suffering from heart failure, and that multiple marker strategies that combine two or more of NGAL, cystatin C, BNP, and serum creatinine can improve this ability to assign risk.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of assigning a risk of an adverse outcome to a patient suffering from heart failure, comprising:

performing two or more of the assay methods in steps (a)-(d) below:

a. an assay method that detects NGAL on a body fluid sample obtained from said patient, thereby providing an NGAL assay result;

b. an assay method that detects one or more of BNP, NT-proBNP and proBNP on a body fluid sample obtained from said patient, thereby providing a natriuretic peptide assay result;

c. an assay method that detects cystatin C on a body fluid sample obtained from said patient, thereby providing a cystatin C assay result;

d. an assay method that detects serum creatinine on a body fluid sample obtained from said patient, thereby providing a serum creatinine assay result; and correlating the assay results obtained to said risk of an adverse outcome.

2. The method according to claim 1, wherein said adverse outcome is mortality, congestive heart failure, or an acute coronary syndrome.

3. The method according to claim 1, wherein, if step (a) is performed, said correlating step comprises comparing said NGAL assay result to a baseline NGAL result, and relating the NGAL assay result to the patient's risk by assigning an increased likelihood of an adverse outcome to said patient when said NGAL assay result is greater than said baseline NGAL result, relative to a risk assigned when said NGAL assay result is less than said baseline NGAL result, or by assigning a decreased likelihood of an adverse outcome to said patient when said NGAL assay result is less than said baseline NGAL result, relative to a risk assigned when said NGAL assay result is greater than said baseline NGAL result; and if step (b) is performed, said correlating step comprises comparing said natriuretic peptide assay result to a baseline natriuretic peptide result, and relating the natriuretic peptide assay result to the patient's mortality risk by assigning an increased likelihood of an adverse outcome to said patient when said natriuretic peptide assay result is greater than said baseline natriuretic peptide result, relative to a risk assigned when said natriuretic peptide assay result is less than said baseline natriuretic peptide result, or by assigning a decreased likelihood of an adverse outcome to said patient when said natriuretic peptide assay result is less than said baseline natriuretic peptide result, relative to a risk assigned when said natriuretic peptide assay result is greater than said baseline natriuretic peptide result; and if step (c) is performed, said correlating step comprises comparing said cystatin C assay result to a baseline cystatin C result, and relating the cystatin C assay result to the patient's mortality risk by assigning an increased likelihood of an adverse outcome to said patient when said cystatin C assay result is greater than said baseline cystatin C result, relative to a risk assigned when said cystatin C assay result is less than said baseline cystatin C result, or by assigning a decreased likelihood of an adverse outcome to said patient when said cystatin C assay result is less than said baseline cystatin C result, relative to a risk assigned when said cystatin C assay result is greater than said baseline cystatin C result; and if step (d) is performed, said correlating step comprises comparing said serum creatinine assay result to a baseline serum creatinine result, and relating the serum creatinine assay result to the patient's mortality risk by assigning an increased likelihood of an adverse outcome to said patient when said serum creatinine assay result is less than said baseline serum creatinine result, relative to a risk assigned when said serum creatinine assay result is greater than said baseline serum creatinine result, or by assigning a decreased likelihood of an adverse outcome to said patient when said serum creatinine assay result is greater than said baseline serum creatinine result, relative to a risk assigned when said serum creatinine assay result is less than said baseline serum creatinine result.

* * * * *